(12) United States Patent
Kemmerer et al.

(10) Patent No.: US 11,617,877 B2
(45) Date of Patent: Apr. 4, 2023

(54) DETECTING PUMP SUCTION, PUMP THROMBUS, AND OTHER ADVERSE VAD MOTOR EVENTS

(71) Applicant: Medtronic, Inc., Minneapolis, MN (US)

(72) Inventors: Michael Kemmerer, Victoria, MN (US); Robert Ecker, Lino Lakes, MN (US)

(73) Assignee: Medtronic, Inc., Minneapolis, MN (US)

(*) Notice: Subject to any disclaimer, the term of this patent is extended or adjusted under 35 U.S.C. 154(b) by 113 days.

(21) Appl. No.: 16/951,037

(22) Filed: Nov. 18, 2020

(65) Prior Publication Data

US 2021/0178038 A1 Jun. 17, 2021

Related U.S. Application Data

(60) Provisional application No. 62/946,535, filed on Dec. 11, 2019.

(51) Int. Cl.
| | |
|---|---|
| *H02P 21/13* | (2006.01) |
| *H02P 6/18* | (2016.01) |
| *A61M 60/515* | (2021.01) |
| *A61M 60/148* | (2021.01) |

(52) U.S. Cl.
CPC ........ *A61M 60/515* (2021.01); *A61M 60/148* (2021.01); *A61M 2205/0294* (2013.01); *A61M 2205/18* (2013.01); *A61M 2205/3365* (2013.01); *A61M 2205/50* (2013.01)

(58) Field of Classification Search
CPC ................ A61M 60/205; A61M 60/50; A61M 2205/04; A61M 2205/18; A61M 2205/3334; A61M 2205/3365; A61M 60/122; A61M 60/148; A61M 60/40
See application file for complete search history.

(56) References Cited

U.S. PATENT DOCUMENTS

| | | | |
|---|---|---|---|
| 6,540,699 B1 | 4/2003 | Smith | |
| 7,139,613 B2 | 11/2006 | Reinke et al. | |
| 7,997,854 B2 | 8/2011 | LaRose et al. | |
| 8,246,573 B2 | 8/2012 | Ali et al. | |
| 8,419,609 B2 | 4/2013 | Shambaugh, Jr. et al. | |
| 8,744,580 B2 | 6/2014 | Doron et al. | |
| 2005/0027323 A1 | 2/2005 | Mulligan et al. | |
| 2006/0229488 A1* | 10/2006 | Ayre ................... | A61M 60/857 600/17 |
| 2012/0130153 A1 | 5/2012 | Bolyard et al. | |
| 2019/0015040 A1* | 1/2019 | Voskoboynikov ... | A61B 5/7278 |
| 2019/0255235 A1 | 8/2019 | Sambelashvili et al. | |
| 2019/0351116 A1 | 11/2019 | Kudlik | |

FOREIGN PATENT DOCUMENTS

WO 9735636 A1 10/1997

OTHER PUBLICATIONS

International Search Report and Written Opinion dated May 18, 2021, for corresponding International Application No. PCT/US2020/061426; International Filing Date: Nov. 20, 2020 consisting of 8-pages.

\* cited by examiner

*Primary Examiner* — Jon Eric C Morales
(74) *Attorney, Agent, or Firm* — Shumaker & Sieffert, P.A.

(57) ABSTRACT

A controller for an implantable blood pump including processing circuitry configured to operate the implantable blood pump and a piezoelectric element in communication with the implantable blood pump.

20 Claims, 3 Drawing Sheets

DETECTING PUMP SUCTION, PUMP THROMBUS, AND OTHER ADVERSE VAD MOTOR EVENTS

CROSS-REFERENCE TO RELATED APPLICATION

This application is related to and claims priority to U.S. Provisional Patent Application Ser. No. 62/946,535, filed Dec. 11, 2019, the entirety of which is incorporated herein by reference.

FIELD

The present technology is generally related to a method and system of detecting adverse events in patients with an implantable blood pump.

BACKGROUND

A mechanical circulatory support device (MCSD) such as a left ventricular assist device (LVAD) is an implantable device that is used to assist the functioning of a failing heart. LVADs include a pump that connects the left ventricle to the aorta which pulls blood from the left ventricle and pumps it into the aorta. With the advent of fully implantable systems having implantable blood pumps, such as LVADs, more electronic equipment is implanted within the body and within or proximate various types of tissue. In particular, transcutaneous energy transfer (TET) systems are used to supply power MCSDs implanted within a human body. An electromagnetic field generated by a transmitting coil outside the body can transmit power across a cutaneous (skin) barrier to a magnetic receiving coil implanted within the body. The receiving coil can then transfer the received power to the implanted heart pump or other internal device and to one or more batteries implanted within the body.

One of the challenges with MCSD's is the potential accumulation of thrombus or suction which can affect pump performance. Currently, external controllers are used to extrapolate the potential presence of adverse events by correlating pump current or voltage feedback to determine potential adverse events such as thrombus or suction.

SUMMARY

The techniques of this disclosure generally relate to method and system of detecting adverse events in patients with an implantable blood pump.

In one aspect, the present disclosure provides a controller for an implantable blood pump including processing circuitry configured to operate the implantable blood pump and a piezoelectric element in communication with the implantable blood pump.

In another aspect of this embodiment, the controller includes a header block, and wherein the piezoelectric element is included in the header block.

In another aspect of this embodiment, the controller includes a driveline in communication with the implantable blood pump, and wherein the piezoelectric element is configured to sense vibrations from the driveline when the implantable blood pump is operating.

In another aspect of this embodiment, the controller is configured to correlate the sensed vibrations into a determination of at least one from the group consisting of a presence and absence of thrombus.

In another aspect of this embodiment, the controller is configured to generate an alert if the presence of thrombus is determined.

In another aspect of this embodiment, the piezoelectric element is a crystal.

In another aspect of this embodiment, the controller includes a driveline in communication with the implantable blood pump, and wherein the piezoelectric element is coupled to the driveline.

In another aspect of this embodiment, the controller is configured to be implanted within a body of a patient.

In one aspect, a method of detecting thrombus in a patient having an implantable blood pump including sensing vibrations from a piezoelectric element coupled to an implanted controller configured to operate the implanted blood pump and correlating the sensed vibrations into a determination of at least one from the group consisting of a presence and absence of thrombus.

In another aspect of this embodiment, the method further includes generating an alert if the presence of thrombus is determined.

In another aspect of this embodiment, the method further includes reducing a speed of the blood pump from a set speed of the implantable blood pump if the presence of thrombus is detected.

In another aspect of this embodiment, the method further includes increasing the speed of the pump back to the set speed if the absence of thrombus is detected.

In another aspect of this embodiment, the piezoelectric element is a crystal.

In another aspect of this embodiment, the implanted controller includes a header block, and wherein the piezoelectric element is included in the header block.

In another aspect of this embodiment, the controller includes a driveline in communication with the implantable blood pump, and wherein the piezoelectric element is configured to sense vibrations from the driveline when the implantable blood pump is operating.

In another aspect of this embodiment, the controller includes a header block, and wherein the piezoelectric element is included in the header block.

In another aspect of this embodiment, correlating the sensed vibrations into a determination of at least one from the group consisting of a presence and absence of thrombus occurs in real time.

In one embodiment, an implantable blood pump system includes a blood pump configured to be implanted within a portion of a mammalian heart. A controller is coupled to the blood pump by driveline. A piezoelectric element is coupled to the controller.

In another aspect of this embodiment, the controller includes a header block, and wherein the piezoelectric element is coupled to the header block.

In another aspect of this embodiment, the controller includes processing circuitry configured to sense vibrations from the piezoelectric element and correlate the sensed vibrations into a determination of at least one from the group consisting of a presence and absence of thrombus.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
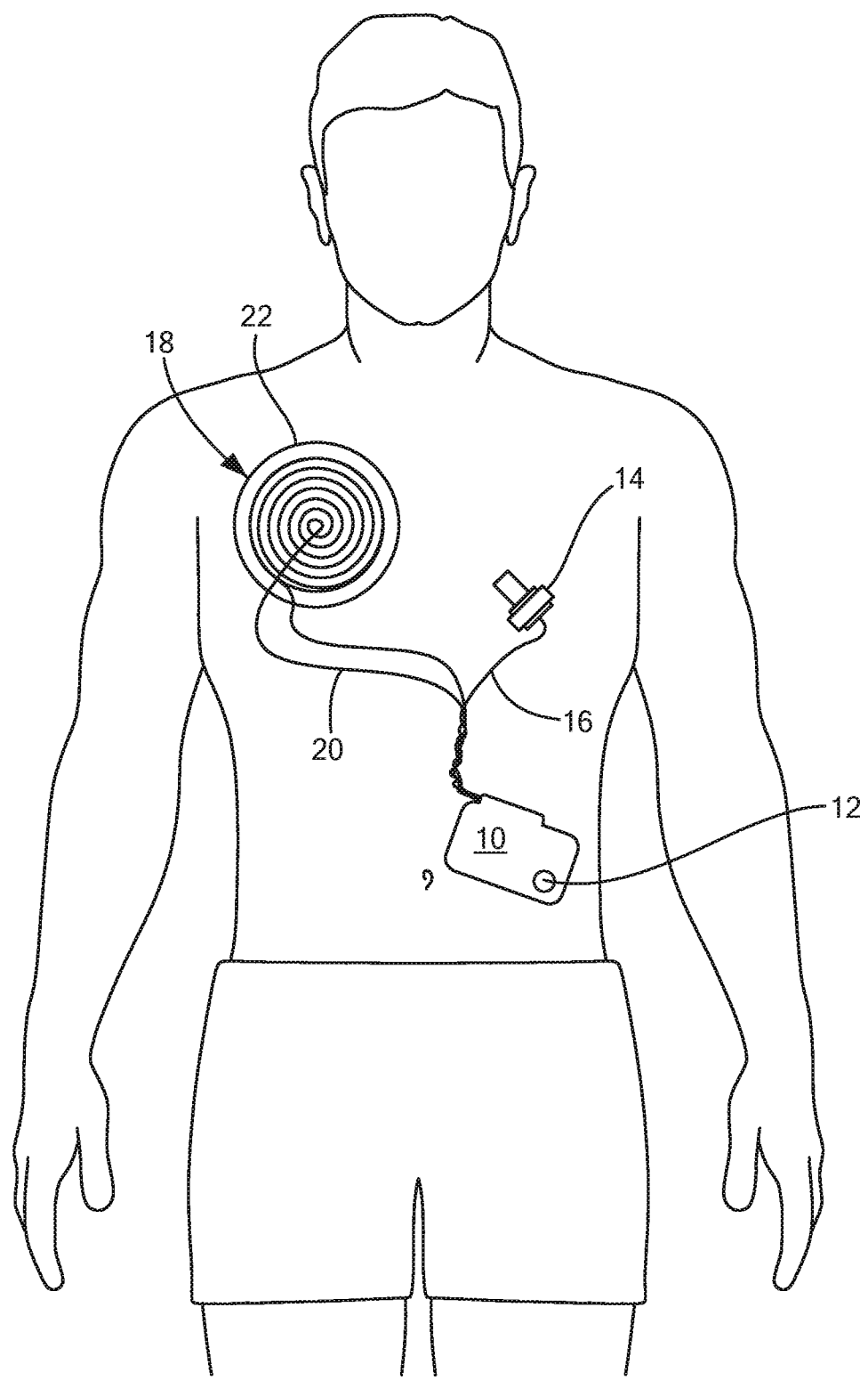
FIG. 1 is a front inside view of a fully implantable blood pump system constructed in accordance with the principles of the present application.

Referring to the drawings in which like reference designators refer to like elements, there is shown in FIG. 1 an exemplary implantable controller for an implantable medical device constructed in accordance with the principles of the present application and designated generally as "10." The controller 10 may include one or more batteries 12 configured to power the components of the controller and provide power one or more implantable medical device, for example, a blood pump such as ventricular assist device (VAD) 14 implanted within the left ventricle of the patient's heart. VADs 14 may include centrifugal pumps, axial pumps, or other kinds of electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference. In an exemplary configuration, the VAD 14 is electrically coupled to the controller 10 by one or more implanted conductors that form a driveline 16 configured to provide power to the VAD 14, relay one or more measured feedback signals from the VAD 14, and/or provide operating instructions to the VAD 14. The controller 10 may include processing circuitry having one or more processors configured to operate the VAD 14 and to processes various signals received from the VAD 14.

Continuing to refer to FIG. 1, a receiving coil 18 may also be coupled to the controller 10 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil (not shown) coupled to an external battery and controller (not shown) disposed opposite the receiving coil 18 on the outside of the patient's body. The receiving coil 18 may be disposed within a hermetically sealed package 22 that does not interfere with the conductivity of the receiving coil 18.

Figure 2:
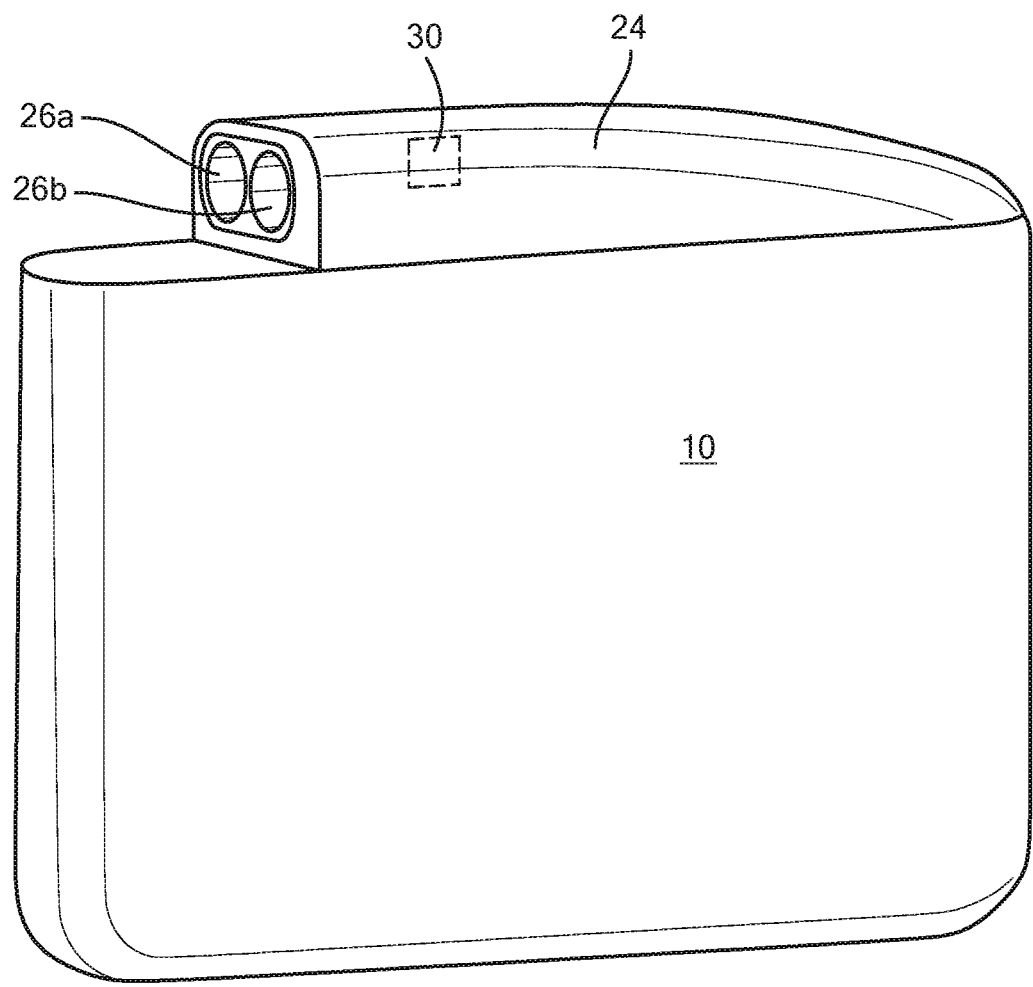
FIG. 2 is a front perspective view of the controller shown in FIG. 1.
Figure 3:
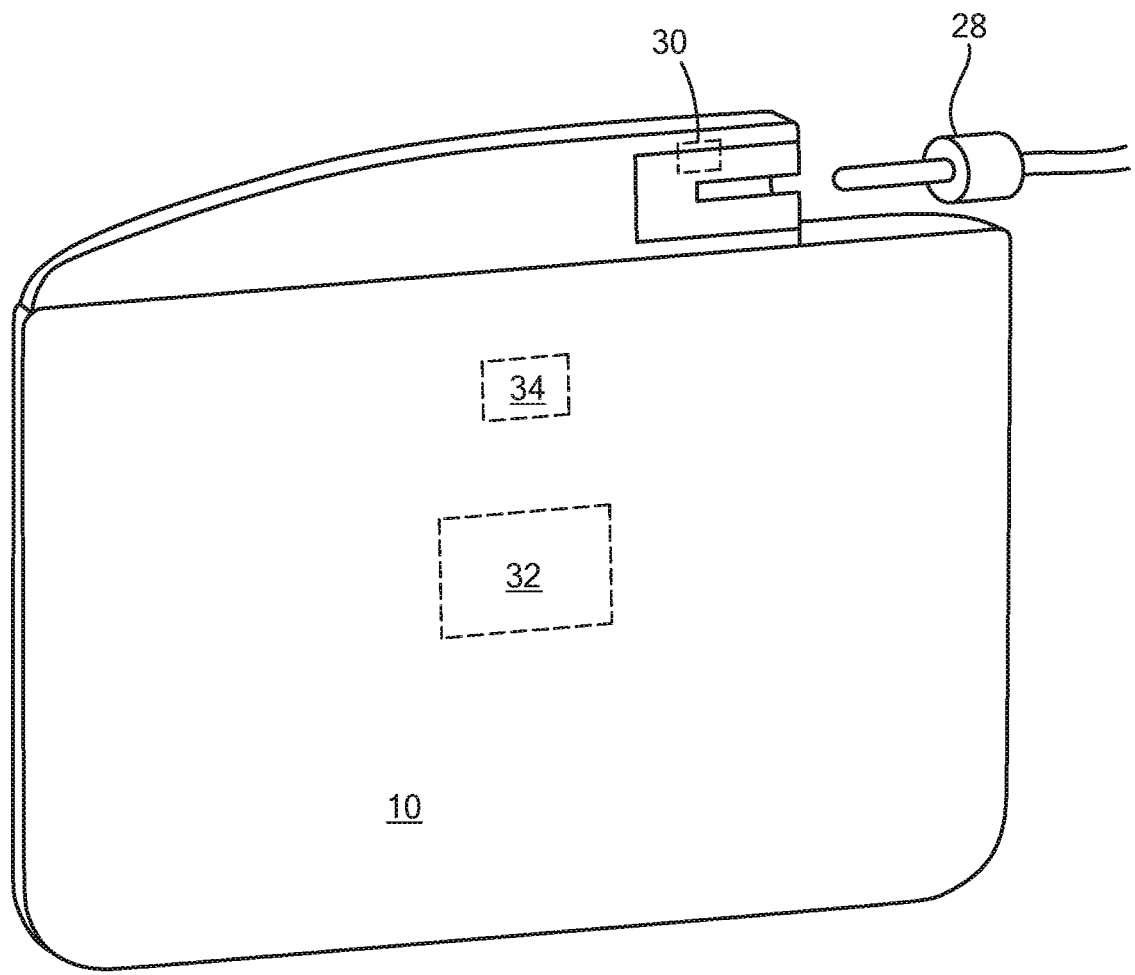
FIG. 3 is an inside cross-sectional view of the controller shown in FIG. 2.

Referring now to FIG. 2, the controller 10 may include a header block 24 sized and configured to receive the driveline 16. In one configuration, the header block 24 includes a port 26a to receive a connector 28 of the driveline 16 and a port 26b configured to receive the one or more implanted conductors 20. Disposed within the header block 24 and hermetically sealed from the exterior on the controller 10 may be a piezoelectric element 30 coupled directly or indirectly to the driveline 16 and/or the connector 28. The piezoelectric element 30 may be a crystal, CMUT, accelerometer, etc., and may be configured to sense vibrations from the driveline 16. In particular, the driveline 16 may vibrate as the VAD 14 is in operation, and those vibrations may be transmitted along the driveline 16 toward the controller 10. During normal operation, the vibrations may have a particular pattern that the piezoelectric element 30 can sense and transduce to an electrical signal readable by the processing circuitry of the controller 10. For example, the piezoelectric element 30 may communicate by the controller 10's processing circuitry by, for example, a two-wire bus as disclosed in U.S. Pat. No. 7,139,613, the entirety of which is incorporated herein by reference. During an adverse event, for example, thrombus or suction, the harmonics in the form of vibrations from the VAD 14 may change and the piezoelectric element 30 can sense those changes in real-time from the driveline 16 that the processing circuitry of the controller 10 can correlate to the presence or absence of an adverse event. For example, the current to the pump may increase in the presence or thrombus or suction to attempt to increase flow from the VAD 14. This increase in current increase the motor speed of the VAD 14, which changes the vibrations of the VAD 14 which are propagated along the driveline 16 toward the controller 10. The piezoelectric element 30 can transduce those vibrations into electrical signals that can be analyzed by the processing circuitry of the controller 10. In one configuration, the processing circuitry may utilize patterns recognition to determine deviations from the known vibration pattern of the VAD 14 and correlate a change in vibration pattern to an adverse event in general or a particular adverse event. For example, thrombus or suction may change the known vibration pattern of the VAD to a vibration pattern that may be programmed into the processing circuitry for recognition. Thus, if a known thrombus or suction vibration patterns is detected by the processing circuitry, an alert may be generated and sent to the external controller and/or a set speed of the VAD 14 may be reduced either by the clinician or automatically. When the suction or thrombus condition is removed, the set speed of the pump may be increased to a predetermined set speed of the pump.

In one configuration, the controller includes an accelerometer 32 in communication with the processing circuitry of the controller 10. The accelerometer 32 may be utilized in conjunction with the piezoelectric element 30 to isolate artifacts from the normal vibration patterns of the VAD 14. For example, if the patient with the VAD 14 is resting, running, or in the shower, the accelerometer can measure those movements and associate any change in the vibration pattern of the VAD 14 with a particular movement to filter that movement's vibrations from the pattern of vibrations. In another configuration, a second piezoelectric element 34 may be included within the controller 10 separate and apart from the piezoelectric element 30 and not connected to the driveline 16. The second piezoelectric element 34 may sense vibrations associated with the controller and/or the external environment separate and apart from the piezoelectric element 30. The vibration patterns measured from the respective piezoelectric elements 30 and 34 may be compared and those vibration patterns not associated with the VAD 14 and the driveline 16 may be filtered to isolate the vibration patterns from the VAD 14.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable blood pump, comprising:
   a piezoelectric element in communication with the implantable blood pump, wherein the piezoelectric element is configured to sense vibrations from the controller when the implantable blood pump is operating; and
   processing circuitry configured to:
      correlate the sensed vibrations into a determination of a presence or an absence of thrombus; and
      modify a speed of the implantable blood pump from a set speed of the implantable blood pump based on the determination of the presence or the absence of thrombus.

2. The controller of claim 1, wherein the controller includes a header block, and wherein the piezoelectric element is included in the header block.

3. The controller of claim 2, wherein the controller includes a driveline in communication with the implantable blood pump, and wherein the piezoelectric element is configured to sense vibrations from the driveline when the implantable blood pump is operating.

4. The controller of claim 1, wherein the processing circuitry is configured to generate an alert if the presence of thrombus is determined.

5. The controller of claim 1, wherein the piezoelectric element is a crystal.

6. The controller of claim 1, wherein the controller includes a driveline in communication with the implantable blood pump, and wherein the piezoelectric element is coupled to the driveline.

7. The controller of claim 1, wherein the controller is configured to be implanted within a body of a patient.

8. The controller of claim 3, wherein the processing circuitry is configured to reduce the speed of the implantable blood pump from the set speed of the implantable blood pump based on the determination of the presence of thrombus.

9. A method of detecting thrombus in a patient having an implantable blood pump, comprising:
   sensing, by a piezoelectric element, vibrations from an implanted controller configured to operate the implanted blood pump, wherein the piezoelectric element is coupled to the implanted controller;
   correlating the sensed vibrations into a determination of a presence or an absence of thrombus; and
   modifying a speed of the implantable blood pump from a set speed of the implantable blood pump based on the determination of the presence or the absence of thrombus.

10. The method of claim 9, further including generating an alert if the presence of thrombus is determined.

11. The method of claim 9, further including reducing the speed of the implantable blood pump from the set speed of the implantable blood pump if the presence of thrombus is detected.

12. The method of claim 11, further including increasing the speed of the pump back to the set speed if the absence of thrombus is detected.

13. The method of claim 9, wherein the piezoelectric element is a crystal.

14. The method of claim 13, wherein the implanted controller includes a header block, and wherein the piezoelectric element is included in the header block.

15. The method of claim 14, wherein the implanted controller includes a driveline in communication with the implantable blood pump, and wherein the piezoelectric element is configured to sense vibrations from the driveline when the implantable blood pump is operating.

16. The method of claim 15, wherein the controller includes a header block, and wherein the piezoelectric element is included in the header block.

17. The method of claim 9, further including correlating the sensed vibrations into the determination of the presence or the absence of thrombus in real time.

18. An implantable blood pump system, comprising:
   an implantable blood pump configured to be implanted within a portion of a mammalian heart;
   a controller coupled to the implantable blood pump by a driveline;
   a piezoelectric element coupled to the controller, wherein the piezoelectric element is configured to sense vibrations from the driveline when the implantable blood pump is operating; and
   processing circuitry configured to:
      correlate the sensed vibrations into a determination of a presence or an absence of thrombus; and
      modifying a speed of the implantable blood pump from a set speed of the implantable blood pump based on the determination of the presence or the absence of thrombus.

19. The system of claim 18, wherein the controller includes a header block, and wherein the piezoelectric element is coupled to the header block.

20. The system of claim 18, wherein the processing circuitry is configured to reduce the speed of the implantable blood pump from the set speed of the implantable blood pump based on the determination of the presence of thrombus.

* * * * *